United States Patent [19]

Everroad

[11] 4,279,508

[45] Jul. 21, 1981

[54] METHOD AND APPARATUS FOR TESTING AIR FILTERS AND THE LIKE

[76] Inventor: Herbert L. Everroad, 9398 Fallen Rock Rd., Conifer, Colo. 80033

[21] Appl. No.: 53,272

[22] Filed: Jun. 29, 1979

[51] Int. Cl.³ .......................................... G01N 21/88
[52] U.S. Cl. .................................... 356/237; 356/241
[58] Field of Search ............... 356/237, 239, 241, 430; 250/562, 563, 572

[56] References Cited

U.S. PATENT DOCUMENTS

| | | | |
|---|---|---|---|
| 3,658,421 | 4/1972 | Shelton | 356/244 X |
| 3,688,780 | 9/1972 | Everroad | 134/21 |
| 3,736,790 | 6/1973 | Pontello | 356/237 X |

FOREIGN PATENT DOCUMENTS 375530  6/1973  U.S.S.R. .................................. 356/237

Primary Examiner—John K. Corbin
Assistant Examiner—Matthew W. Koren
Attorney, Agent, or Firm—Wm. Griffith Edwards

[57] ABSTRACT

An apparatus for testing paper air filters and the like for leaks or holes comprises an arrangement for positioning an electric lamp on one side of the filter to provide a bright light and inspecting the filter for holes by observing it from the opposite side. A motor is provided for moving the light to selected positions along the filter. The inspection of the filter is effected by use of an electronic light image intensifier which makes possible the quick and reliable detection of very small holes in the paper.

13 Claims, 3 Drawing Figures

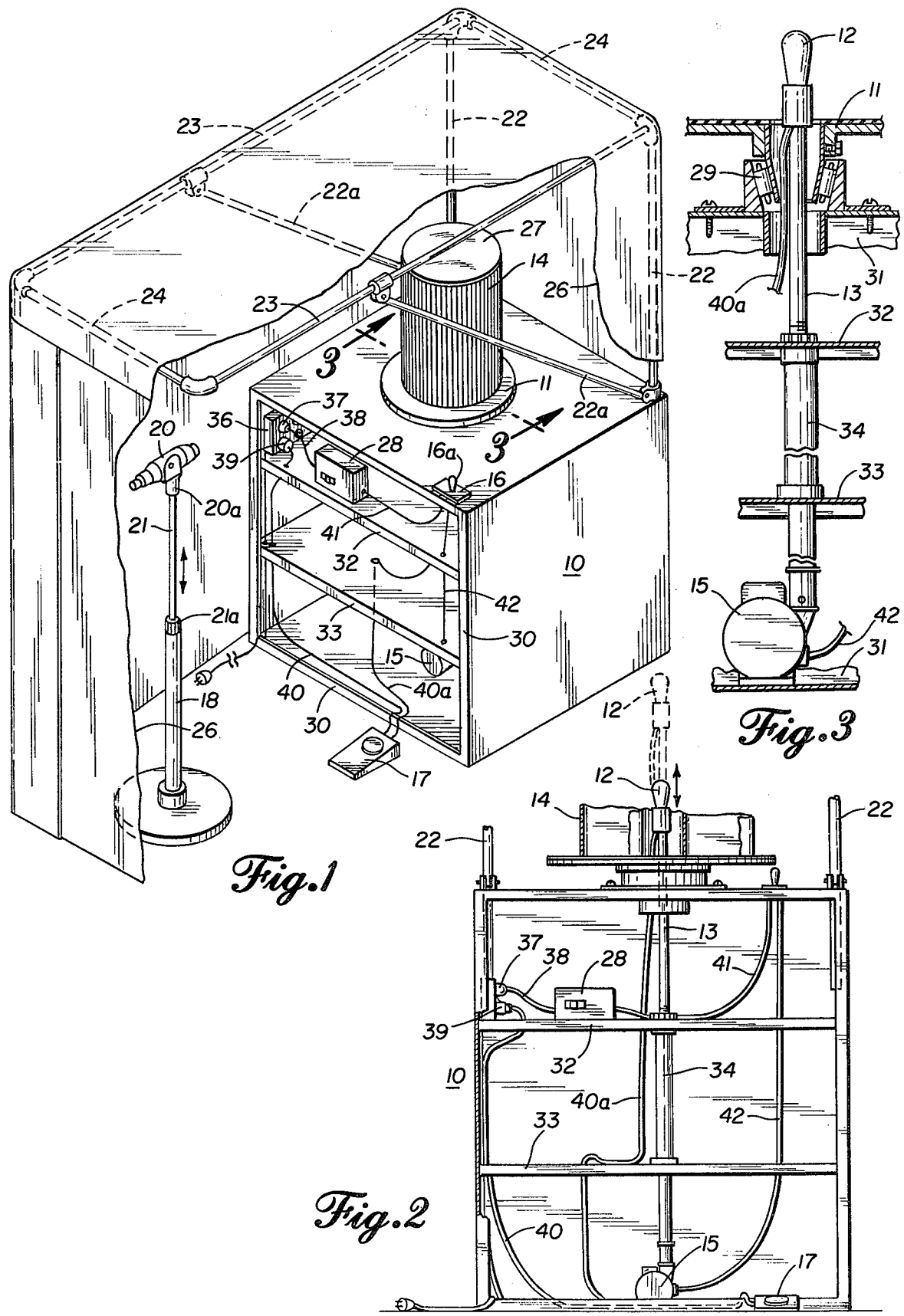

METHOD AND APPARATUS FOR TESTING AIR FILTERS AND THE LIKE

This invention relates to the testing of paper air filters and similar porous material and the like for the detection of holes therein and particularly to an improved method and apparatus for utilizing light for such testing purpose.

BACKGROUND OF THE INVENTION

The accordion folded paper air filters used for cleaning the air supplied to internal combustion engines become clogged by the accumulation of dust and other matter removed from the air. It has been found to be practical and highly economical to clean the filters on large engines so that they may be used a number of times instead of being discarded after becoming clogged. Apparatus has been provided for the quick and effective cleaning of such filters and, by way of example, one form of such apparatus is disclosed in U.S. Pat. No. 3,688,780, granted Sept. 5, 1972, to Herbert L. Everroad. In order to avoid the loss of time and expense in the cleaning of filters having holes therein rendering them ineffective, it has become a regular practice to inspect the filters for imperfections or flaws to determine their effectiveness for reuse before subjecting them to the cleaning process. One method which has been used for such inspection is to brush off any heavy deposits of dust or other material and to position a bright light on one side of the filter and to watch on the other side for any light penetration; the light is moved about until a defect is found or until the entire filter has been inspected. While this method has been effective for detecting a great many defective filters, it has not been fully effective for detecting very small but disabling holes in many filters. Accordingly, it is an object of the present invention to provide an improved method and apparatus employing light for the detection of holes in porous media including air filters and the like.

It is another object of this invention to provide an improved apparatus and method for detecting holes in filters and the like which is quick and highly effective for the detection of holes including extremely small holes.

It is another object of this invention to provide an improved method and apparatus utilizing light for the detecting of holes in paper filters and the like with increased speed and effectiveness.

It is a further object of this invention to provide an improved method and apparatus for detecting holes or imperfect seals in air filters and the like as manufactured or after use.

SUMMARY OF THE INVENTION

Briefly, in carrying out the objects of this invention in one embodiment or mode thereof, a cabinet or counter is provided with a rotatable plate on which a cylindrical air filter may be placed with its axis upright. A light source is mounted on a support movable along the vertical axis and a motor drive is provided to move the light source along the axis. A darkened room is provided about the apparatus and the filter is inspected by use of an electronic light image intensifier positioned to view a portion of the filter between the light and the observer. The light source positioning drive is controlled by a forward and reverse switch readily accessible to the observer. Energization of the source is effected by a foot operated switch. The observer thus may inspect the filter along its length and then turn it to another position for inspection until the entire filter has been inspected or a flaw detected.

The features of novelty which characterize this invention are pointed out with particularity in the claims annexed to and forming a part of this specification. This invention itself, however, together with further objects and advantages thereof, will best be understood upon reference to the accompanying drawings taken in connection with the following detailed description of the disclosed embodiment of the invention.

BRIEF DESCRIPTION OF THE DRAWINGS

FIG. 1 is a perspective view, partly broken away, of an apparatus embodying the invention;

FIG. 2 is a front elevation view of the apparatus; and

FIG. 3 is a sectional elevation of the central portion of the apparatus taken along the line 3—3 of FIG. 1.

DESCRIPTION OF THE PREFERRED EMBODIMENT

Referring now to the drawings, FIGS. 1 and 2 illustrate an apparatus for inspecting cylindrical accordion-folded paper filters including a rectangular cabinet 10 which is open on the front side and has a rotatable table 11 mounted on the top. An electric lamp 12 is mounted on a supporting shaft or rod 13 positioned along the central axis of the table 11 for movement up and down; thus, when a cylindrical filter 14 is placed on the rotating table the lamp may be moved to selected positions along the length of the cylinder. The lamp assembly is mounted to be moved up and down by operation of a motor 15 supported within the cabinet and connected upon operation to drive the shaft 13 either up or down selectively. The filter 14 when mounted on the table 11 may be rotated to selected positions so that the lamp may be made to illuminate selected vertical sections of the filter. The motor 15 may be controlled by a spring-biased switch 16 having a handle 16a which is biased to its central open position and may be moved toward a forward or a reverse running position to raise or lower the shaft 13. The energization of the lamp is controlled by a foot pedal actuated switch 17 shown adjacent a weighted stand 18 on which an optical device 20 is mounted. The device 20 is mounted on the top of a shaft 21 by a bifurcated fitting 20a in which the device is rotatable about a horizontal axis, the fitting being rotatable about the end of the rod 21. The rod is secured on the base 18 by a clamping fitting 21a which may be loosened to allow the rod to slide to a selected position and then is tightened to hold the rod securely. Thus, the device 20 may easily be positioned at desired levels and held in each selected position, the device then being movable universally to scan a selected area of the filter 14. A light metal frame structure is provided about the apparatus comprising vertical corner posts 22 secured to the back corners of the cabinet 10 and top horizontal members 23 and 24 forming a rectangular frame which is held in a horizontal position by diagonal braces 22a. Roof and side curtains 25 and 26, respectively, are supported on the frame to provide a darkened room during use of the apparatus, the curtains being broken away in the drawing to show the apparatus within.

During use of the apparatus when a filter has been placed on the table 16 a cover plate 27 is placed over the top end of the filter to act as a light shield. Assuming that the lamp is in its uppermost position, the operator then operates the foot switch to energize the lamp and in looking through the optical device 20 scans the area of the filter between the lamp and the device. Any holes in the filter will allow light to pass through and large holes, of course, can be detected by the naked eye. The purpose of the device 20 is to detect even minute openings which, however, are sufficiently large to afford the passage of undesirable abrasive particles. The filters are required, by way of example, to remove fine particles of sand or other grit-like material which can cause severe damage to the moving parts of an engine. It may be desirable, for example, that particles larger than, say, about fifty microns be removed by the filter. Thus, it is necessary that very small openings be detected when testing the filter in order that filters having holes of a size greater than say fifty microns will be removed from service. In order to detect light passing through these extremely small openings, the optical device 20 is employed. This optical device is a monocular viewer provided with an image intensifier which accepts light of various wavelengths and converts it to electrons through a photocathode. The electrons thus produced are few and of low energy and the device uses an electron amplifier for the purpose of transforming a low visibility image to a high visibility image. The electron beam is converted to visible light by use of a phosphor screen. A device of this type designated Litton Model M826 monocular is sold by the Electro-Optics Department, Electron Tube Division, of Litton Industries. The monocular 20 may be mounted on the base 18 as shown in the drawing or may be held in the operator's hand during the course of the test. The high intensification of the image makes it possible for the operator to detect light changes caused by very small openings in the filter material and in the event the operator locates an opening it will enable him to determine its relative size and when it exceeds a selected minimum value informs the operator that the filter is defective and must be replaced. Each scanning of the filter covers a substantial area so that the operator may move, say, from top to bottom over several selected scanning areas then rotate the filter and repeat the scanning for another vertical pass until the entire filter has been inspected or an unacceptable perforation detected. The switch 16 which is arranged to lower the lamp in one position and to raise it in the other enables the operator to position the lamp easily and then to control the on and off period of the lamp by the foot switch while he is observing the filter through the monocular 20.

The monocular presents an enlarged and optically brighter view of holes through which light passes and the operator may calibrate the device, by way of example, by piercing a test filter with a pin or needle to produce a hole of a selected size representing the maximum acceptable penetration. By observing the resulting image the operator will know the approximate limiting size opening as shown in the device and can reject any filter found to have a larger opening as indicated by the light image.

It has been found that a monocular device of this type can detect very low intensities of light and that the light penetrates material such as paper sufficiently to produce a substantially uniform lighting of the phosphor screen. When the light passes through two or more layers of paper or the like, a hole in any one of the layers will produce a corresponding optical effect; thus, the presence of holes anywhere in the layers under examination can be detected. A direct hole through the material which allows a light beam to pass produces a correspondingly bright image on the screen. The method of this invention, thus is useful for testing paper air filters either new or used, and also may be used for testing paper and other porous materials of many kinds for detecting holes or damaged or defective areas therein.

The motor 15 for raising and lowering the lamp is a reversible DC motor and it has been found that such motors which are provided for raising and lowering automobile radio antennas and which operate at 12 volts are highly suitable for this purpose. For this reason, a converter 28 is provided to produce a 12 volt output from the 115 volt house current. The staff 13 on which the lamp 12 is mounted is attached to the top of the antenna member and it has been found that this provides a highly satisfactory arrangement for moving the lamp as required for the test.

As shown in FIG. 3, table 16 is mounted on roller bearings 29 which make it easily turnable. Quick and easy adjustment of the filter to required positions is thus provided and the testing time is reduced by the ready manipulation of the filter under test.

The cabinent 10 has been shown as constructed of sheet metal, the front opening being formed with a flange 30 extending about the opening from the top, bottom and side walls. The back wall is solid as indicated by the top and bottom broken portions thereof shown at 31 in FIG. 3. Upper and lower flanged shelves 32 and 33, respectively, are provided within the cabinet. The converter 28 is mounted on the upper shelf and both shelves support a cylindrical tube lamp assembly drive and the lower end of the shaft 13.

The electrical circuitry for the lamp 12 and the motor 15 is indicated generally in FIGS. 1 and 2. A power supply plug 35 is provided to supply, say, 115 volts AC power, to a connection block 36 to which the converter 28 is connected by a plug 37 and cord 38, and the lamp 12 and switch 17 are connected by a plug 39 and a cord 40, the switch being connected to the lamp by a cord 40a which is of sufficient length and flexibility to afford free vertical movement of the lamp with the shaft 13. The converter 28 is connected to the switch 16 and the motor 15 by leads 41 and 42. The cords 40 and 40a are flexible and sufficiently long to allow the foot pedal 17 to be positioned for the observer's convenience. The switch 16 is mounted near the front edge of the cabinet so that it may easily be reached by the observer when the height of the lamp is to be adjusted to a different level. The lamp 12 in its lowermost position is retracted into a sleeve or collar 43 secured to the table 11, and which carries the inner race of the roller bearings 29, the outer race being mounted on the top of the cabinet.

The curtain 26 is provided with overlapping edge portions (not shown) which provide a door adapted for an observer's use when entering or leaving the darkened area.

It will readily be apparent that the method employed in this testing apparatus may be utilized for testing various types of filters, both those similar to the illustrated cylindrical accordion paper filter and flat filters, it merely being necessary to place the filter between the lamp and the monocular observing device and to shield the testing zone from undesired light. The amplification which may be effected by the monocular may range from zero to 20,000 lumens gain and any light rays passing through the filter will be greatly enlarged to show the imperfection. The apparatus is effective for this purpose whether the paper is new or is old and dirty.

The apparatus and method of this invention make possible the optical testing of paper filters and the like to detect very small holes. Filters may be tested rapidly and the detection of a defective filter is quick and positive and this enables an operator to test filters one after another more quickly and more efficiently.

While the invention has been described in connection with a specific embodiment various other applications and modifications will occur to those skilled in the art. Therefore, it is not desired to limit the invention to the specific embodiment or mode illustrated and described, and it is intended, by the appended claims to cover all modifications and modes within the spirit and scope of the invention.

I claim:

1. The method of testing air filter paper and similar materials for holes which comprises:
    positioning a light source on the far side with respect to the observer of a portion of the paper to be tested,
    energizing the light source,
    providing a light image amplifying electronic optical observation device, and
    scanning with the optical device the area of the paper between the light source and the test observer to detect light penetration therethrough.

2. The method of testing set forth in claim 1 including the step of marking the area of any light penetration detected during the scanning.

3. The method of testing set forth in claim 1 including the step of moving the light source to a different test position and repeating the steps of test.

4. The method of testing set forth in claim 1 wherein the material is that of a cylindrical air filter and wherein the light source is located within the cylinder, and including the steps of
    moving the light source to successive positions with respect to the axis of the cylinder, repeating the steps of the test in each position, and thereafter rotating the cylinder to a second position and repeating the test in a second series of like successive positions of the light source.

5. The method of testing set forth in claim 3 or claim 4 including the step of discontinuing the test in the event of light penetration in excess of a predetermined minimum.

6. The method of testing set forth in claim 4 including the repeating of the rotating of the cylindrical filter to successive positions and repeating the steps of the test until the entire cylindrical filter has been tested.

7. An apparatus for testing air filters and the like to locate holes therein which comprises:
    rotatable means for supporting a cylindrical air filter to be tested in an upright position and for rotation about its central axis,
    a light source,
    means for supporting said light source for movement along the central axis of said rotatable means, and
    motor-actuated means for moving said supporting means along said axis to locate said light source in selected positions.

8. An apparatus for testing air filters and the like as set forth in claim 7 or claim 1 including means for shielding the zone about the filter and said device from ambient light.

9. An apparatus for testing air filters and the like to locate holes therein which comprises:
    means for supporting an air filter to be tested,
    a light source,
    means for supporting said light source on one side of the filter to be tested,
    an electronic image amplifying optical device adapted to be positioned on the side of the filter opposite that of said light source for amplifying light passing through the filter, and
    means for shielding the zone about the filter and said device from ambient light.

10. An apparatus for testing air filters and the like as set forth in claim 9 including motor-actuated means for moving said light source to selected positions along the filter.

11. An apparatus for testing air filters and the like as described in claim 9 or claim 10 wherein said shielding means provides sufficient room to house an observer, and including
    remote control means adapted for operation by the observer to control the energization of said light source while said observer is at a substantial distance from the filter.

12. An apparatus for testing air filters as set forth in claim 11 wherein the motor of said motor-actuated means is an electric motor and including a control switch movable from its open position to a first position for forward movement of said light source and to a second position for retracting movement of said light source.

13. An apparatus for testing air filters and the like as set forth in claim 7, including remote control means adapted for operation by an observer to control the energization of said light source while said observer is at a distance from the filter.

* * * * *